United States Patent [19]

Nummy

[11] Patent Number: 4,772,713
[45] Date of Patent: Sep. 20, 1988

[54] QUATERNARY PYRIDINE SALTS USEFUL FOR PREPARATION OF 4-SUBSTITUTED PYRIDINES

[75] Inventor: Laurence J. Nummy, New Burh, N.Y.

[73] Assignee: Nepera, Inc., Harriman, N.Y.

[21] Appl. No.: 52,330

[22] Filed: May 21, 1987

Related U.S. Application Data

[62] Division of Ser. No. 691,786, Jan. 16, 1985, Pat. No. 4,672,121.

[51] Int. Cl.$^4$ ............... C07D 213/84; C07D 213/71; C07D 213/68; C07D 401/06
[52] U.S. Cl. .................. 546/286; 546/193; 546/275; 546/281; 546/291; 546/309; 546/336; 540/481; 540/597
[58] Field of Search ........... 546/286, 291, 193, 309, 546/281, 275, 336; 540/481, 597

[56] References Cited

U.S. PATENT DOCUMENTS

| | | | |
|---|---|---|---|
| 2,857,310 | 10/1958 | Heininger | 514/311 |
| 3,079,394 | 2/1963 | Dowbenko | 546/108 |
| 3,235,449 | 2/1966 | Thomas et al. | 546/290 |
| 3,260,723 | 7/1966 | L'Italien et al. | 546/290 |
| 3,689,470 | 9/1972 | Shachat et al. | 526/312 |
| 4,158,093 | 6/1979 | Bailey et al. | 546/193 |
| 4,220,785 | 9/1980 | Oude Alink et al. | 546/349 |

OTHER PUBLICATIONS

Klingsberg, Erwin, "Heterocyclic Compounds, Pyridine and Derivatives", Part 1, Chaptr. 1 & 2, Part 2, Chaptr. 3–8, Interscience Pub., N.Y. 1960.

Primary Examiner—Mary C. Lee
Assistant Examiner—Dale A. Bjorkman
Attorney, Agent, or Firm—Millen & White

[57] ABSTRACT

Disclosed are compounds of the formula

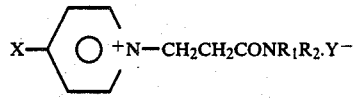

wherein $R_1$ and $R_2$ independently are H or $C_{1-8}$-alkyl or together are $C_{2-7}$-alkylene forming a ring with the connecting N-atom; X is CN, halo, $C_{6-10}$-arylsulfonyl, $C_{6-10}$-arylsulfinyloxy, $C_{6-10}$-aryloxy, $C_{6-10}$-arylthio or $C_{1-8}$-alkylsulfonyloxy or nitro, and Y is the anion of an acid having a p$K_a$ of about 3 or less.

These compounds are intermediates in the preparation of 4-substituted pyridines.

5 Claims, No Drawings

QUATERNARY PYRIDINE SALTS USEFUL FOR PREPARATION OF 4-SUBSTITUTED PYRIDINES

This is a division of application Ser. No. 691,786, filed Jan. 16, 1985, now U.S. Pat. No. 4,672,121.

BACKGROUND OF THE INVENTION

This invention relates to a process for preparing 4-substituted pyridines from other starting 4-substituted pyridines.

The ability to modify a particular pyridine derivative resulting in the formation of a second pyridine derivative is sometimes highly desirable. Particularly important modifications of pyridine derivatives are in three categories: (1) nucleophilic substitution of a suitable leaving group at the 2- or 4-position of the pyridine ring; (2) electrophilic substitution of an alkyl group at the 2- or 4-position of the pyridine ring; and (3) oxidative coupling of a pyridine derivative to produce a bipyridine.

The prior art describes many approaches to the solution of this general problem. For industrial purposes, the primary motivation for selecting the optimum pathway is usually a combination of availability of the first derivative and the cost effectiveness of the route used to convert it to the second derivative. This greatly reduces the number of options currently available. An appreciation for the inadequacy of the technology in this area, bearing in mind the above constraint, can be obtained from a brief survey of the literature.

The most expedient strategy for substituted pyridine transformations is direct exposure of the free base to the appropriate reagents. In the case of 2- or 4-picoline, activation of a methyl group toward electrophilic attack requires the use of very strong bases such as alkyl lithium compounds, sodamide or Lewis acids such as zinc chloride in combination with high temperature. Analogously, direct displacement of a suitable leaving group at the 2- or 4-position on the ring of a pyridine base demands extreme conditions. For example, conversion of 2-bromopyridine to 2-aminopyridine in 57% yield requires heating at 200° C. with ammonium hydroxide under pressure. (Den Hertog et al, Rec. Trav. Chim. 51, 381 (1932).) Dimethylamine reacts with 4-chloropyridine under pressure at 150° C. (L. Pentimalli, Gass. Chim. Ital., 94, 902 (1964).) Sodium or potassium amide and metal methyl anilides can be used successfully in etheral solvents or liquid ammonia but this approach is not practical on an industrial scale. (Hauser, J. Org. Chem., 15, 310 (1949).)

In addition to these considerations, accessibility of starting materials can also be a problem. Successful displacement reactions have been carried out in good yield with a variety of nucleophiles using N-pyridyl-4-pyridinium chloride hydrochloride or 4-phenoxypyridine as substrates. (D. Jerchel et al, Chem. Ber., 91, 1266 (1958).) These materials are not commercially available in bulk quantities which necessitates a separate synthesis. Moreover, the former substrate gives low yields in reactions with primary alkylamines. This is circumvented by using 4-phenoxy-pyridine; however, this material is even further removed from commercially available pyridine derivatives.

Another strategy which can be applied to the transformation of one pyridine derivative into another involves an activation-modification-deactivation sequence. Two methods of achieving this are known, namely, by taking advantage of the intermediacy of either the pyridine N-oxide of the initial pyridine derivative or its quaternary salt. It is well-documented that converting a pyridine compound to either of these two types of derivatives greatly enhances the reactivity of the 2- and 4-ring positions toward nucleophilic attack followed by expulsion of a leaving group if present. Furthermore, if an alkyl group is present at one of these positions, exposure of the quaternary salt to mild bases such as an alkylamine, or potassium ethoxide in the case of the N-oxide, is sufficient to initiate anhydro base formation resulting in a condensation or addition if an electrophile is present.

There are drawbacks to using a pyridine N-oxide in this scheme. These materials are usually less available than the pyridine precursor, and they require a synthesis and isolation prior to being carried through subsequent reactions. The degree of activation imparted by the N-oxide group is not as great as that of quaternary salt formation and reaction conditions, for example in substitution reactions with amines, are still vigorous. 4-chloropyridine-N-oxide undergoes reaction with diethylamine at 135° C. in a sealed tube to produce the 4-substitution product in 47% yield, and the same reaction with morpholine occurs at 130° C. to give a 53% yield of the analogous product. There is also the added obligation to reduce the N-oxide function in order to obtain the desired pyridine base.

Quaternary salt formation imparts the greatest reactivity to the 2- and 4-substituents of the pyridine ring. Consequently, more economical and available 4-pyridines, e.g., 4-cyanopyridine, can be quaternized with methyliodide, for example, and reacted with ammonia (Metzger et al, J. Org. Chem. 41 (15), 2621 (1978)) in preference to using a halopyridine. The conditions under which these salts are formed also offer the greatest potential for further reaction without isolation of intermediates. The milder reaction conditions possible as a result of greater reactivity combined with the ability to use these quaternary salts without isolation would present an attractive opportunity for processing one pyridine base into another if one final obstacle could be overcome. The difficulty is in the dequaternization of the newly formed pyridine quaternary salt.

The prior art describes several procedures for dealkylating the methyl quaternary salts of pyridine bases. These involve such reagents as triphenylphosphine/dimethylformamide at reflux (Aumann et al, J. Chem. Soc. Chem. Commun., 32 (1973), triphenylphosphine/acetonitrile (Kutney et al, Synth. Commun., 5 (2), 119 (1975) and diazabicyclononane/dimethylformamide or thiourea (Ho, Synth. Commun., 3, 99 (1973)). All of these methods have serious problems associated with implementing them in a convenient and economical industrial preparation. The problems include cost of reagents, difficulty in recycling them and low yields and/or long reaction times in some cases.

A partial solution to the problems discussed above has been addressed in U.S. Pat. No. 4,158,093. A pyridine base is first quaternized with 2- or 4-vinylpyridine to give a pyridylethyl quaternary salt which is then converted into the quaternary salt of a new pyridine base by one of the three types of reactions described above. The new salt is subsequently converted to the desired pyridine base by dequaternization using sodium hydroxide. The co-product is vinylpyridine which is recovered and recycled.

The methodology, though an improvement over prior procedures, is not free of other disadvantages. For instance, the vinylpyridine co-product formed along with the desired pyridine derivative must be recovered and recycled in order to achieve a process which is economically practical. Over and above economic considerations, this can present operational problems. Vinylpyridines have physical properties similar to other pyridine bases. The most convenient method of separation is by distillation which is laborious in cases where the boiling point of the new pyridine base is close to that of the vinylpyridine produced. Even when this is not the case, avoiding this extra step is preferable.

Another drawback to this method is the use of large excesses (as high as 30 mole equivalents in one case) of sodium hydroxide in order to effect dequaternization of the intermediary pyridinium salt. This adds to the cost of the process by increased usage of raw materials, lowered product throughput and greater quantities of chemical waste to be treated and disposed of.

Consequently, the problem remains to provide a more advantageous process for preparing 4-substituted pyridines, preferably by a quaternization-modification-dequaternization sequence.

SUMMARY OF THE INVENTION

It is an object of this invention to provide a process for preparing 4-aminopyridines by a quaternization-modification-dequaternization scheme applied to starting material 4-pyridines.

It is another object of this invention to provide such a process which can be effected under moderate conditions rendering it amenable to industrial use.

It is yet another object of this invention to provide such a process which can be effected using inexpensive and readily available starting materials.

It is a further object of this invention to provide such a process wherein, in the dequaternization step, the desired product is readily separable from the reaction medium.

It is still a further object of this invention to provide such a process wherein the quaternization reagent need not be recycled for economic considerations.

Upon further study of the specification and appended claims, further objects and advantages of this invention will become apparent to those skilled in the art.

These objects have been achieved by providing a process for preparing a 4-substituted pyridine product from a starting pyridine substituted in the 4-position by a leaving group susceptible to nucleophilic displacement when the starting pyridine is quaternized, comprising, quaternizing the starting pyridine, with acrylamide, N-monoalkylacrylamide or N-dialkylacrylamide under effective acidic conditions; subjecting the resultant, corresponding quaternized starting pyridine to a nucleophilic displacement reaction with a reagent which reacts to produce the corresponding 4-substituted pyridine; and dequaternizing the latter under effective basic conditions to liberate the desired 4-substituted pyridine product.

These objects have further been achieved by providing compounds of the formula

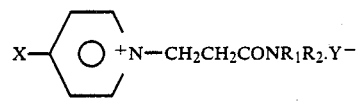

wherein $R_1$ and $R_2$ independently are H or $C_{1-8}$-alkyl or together are $C_{2-7}$-alkylene forming a ring with the connecting N-atom, X is CN, halo, $C_{6-10}$-arylsulfonyl, $C_{6-10}$-arylsulfinyloxy, $C_{6-10}$-aryloxy, $C_{6-10}$-arylthio, $C_{1-8}$-alkylsulfonyloxy or nitro, and Y is the anion of an acid having a $pK_a$ of about 3 or less, preferably 1 or less.

DETAILED DISCUSSION

This invention involves the preparation of the 2-carbamoylethyl pyridinium salt (optionally N-substituted by alkyl in the carbamoylethyl group) of a suitable starting pyridine base, followed by reaction of the latter with a nucleophilic reagent to produce the corresponding 2-carbamoylethyl quanternary salt of the nucleophilic substituted pyridine starting material. The latter is then treated with a basic material causing dequaternization, thereby liberating the new 4-substituted pyridine. The reaction is illustrated below for 4-cyanopyridine and acrylamide.

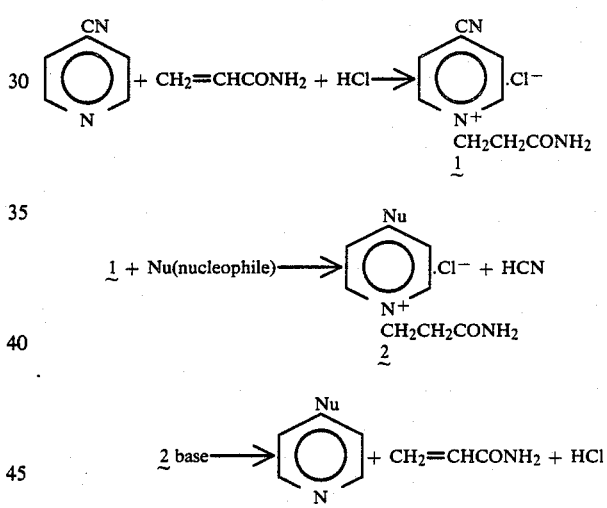

The reaction is further illustrated below for 4-chloropyridine, acrylamide, dimethylamine, and sodium hydroxide to make 4-dimethylamino pyridine 5.

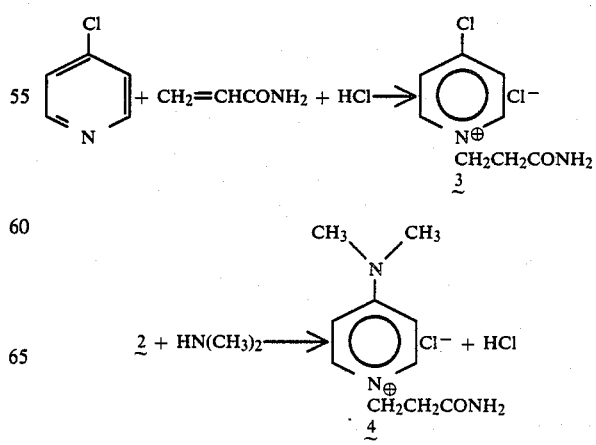

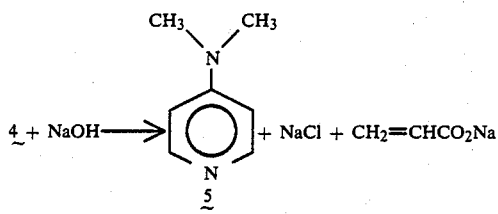

In this process, the disadvantages of the prior art are avoided and/or ameliorated. For example, there is no necessity to recover and recycle the quaternization reagent. Furthermore, in the dequaternization reaction which liberates the new pyridine product, the coproduct, i.e., the quaternizing agent, has physical properties very different from those of the pyridine product, thereby significantly facilitating isolation of the latter in high purity by simple extraction. Distillation techniques are not necessary.

Another significant improvement is derived from the shorter reaction times and lower temperatures necessary to carry out both the quaternization and dequaternization reactions. In addition, the latter is carried out using a smaller amount of a milder caustic reagent. Furthermore, as further explained below, in many situations, the process of this invention can be carried out on isomeric mixtures of a readily available pyridine starting material with the modification reaction proceeding only on the desired isomer. In this way, only the desired 4-substituted product will be prepared, greatly simplifying the isolation of the desired material from the final reaction medium.

The quaternization reaction can be carried out using the preferred acrylamide or also an alkylacrylamide ($CH_2=CH-CO-NR_3R_4$) as the quaternizing reagent. N-$C_{1-8}$alkylacrylamides ($R_3=H$, $R_4=C_{1-8}$-alkyl), N,N-di-$C_{1-8}$alkylacrylamides ($R_3/R_4=C_{1-8}$-alkyl) and cyclic such amides ($R_3/R_4$ together form a ring, e.g., together are $C_{2-7}$-alkylene bonded to the N-atom) are suitable. Of course, other equivalent reagents apparent to skilled workers are included within the scope of this invention.

For example, it has been determined that starting material pyridines quaternized by $-CH_2CH_2-COOH$ will also provide similar advantages in the subsequent modification and dequaternization steps. The use of such quaternary pyridine salts, or their equivalent ester salts, e.g., $C_{1-8}$-alkylesters, is also included within the scope of this invention. These are readily preparable using any of the many conventional, well known methods for converting amides to the corresponding carboxylic acids or esters, e.g., by routine reaction with aqueous ethanol and hydrochloric acid. Conditions suitable for this version of the invention are essentially the same as those discussed below with respect to the carbamoylethyl quaternizing groups, precise optimum conditions being routinely determinable in accordance with this disclosure, perhaps in conjunction with a few preliminary experiments.

The reaction of acrylamide with substituted pyridines has been carried out in the past as an isolated reaction, per se. See, e.g., R. Dowbenko, J. Org. Chem., 25, 1123 (1960). These reactions were conducted with pyridine itself and also picolines. However, there was no suggestion in the prior art that, this quaternization reaction would be useful in a quaternization-modification-dequaternization scheme.

Suitable starting material pyridines are those substituted in the 4-position with any of the wide variety of well known leaving groups susceptible to subsequent nucleophilic displacement. These include cyano, halo (fluoro, chloro, bromo, iodo), $C_{6-10}$-arylsulfonyl (optionally substituted by $C_{1-4}$-alkyl), $C_{6-10}$-arylsulfinyloxy, $C_{1-8}$-alkylsulfonyloxy, $C_{6-10}$-aryloxy (e.g., phenoxy), $C_{6-10}$-arylthio (e.g., phenylthio), nitro, etc. All of the substituents are located in the 4-position since experiments have shown that 2-substitution and 3-substitution are not applicable. Because of this fact, the process of this invention can be used in conjunction with mixtures of 2- and/or 3-substituted pyridines with the desired 4-substituted pyridine and, yet, only the latter will undergo the nucleophilic displacement reaction to produce the desired substituted pyridine. This is a special advantage when isomeric mixtures are the least expensive starting materials. At the completion of the reaction, the desired 4-substituted pyridine can readily be separated.

The quaternization is carried out in the presence of an acid of sufficient strength to catalyze the reaction. Typically, the acid will have a $pK_a$ of less than about 3. The pH of the reaction solution will generally be in the range of about 1-4. Suitable strong acids include inorganic or organic ones. Examples include HCl, HBr, HI, sulfuric acid, phosphoric acid, HSCN, trifluoroacetic acid, trichloroacetic acid, picric acid, etc. Suitable reaction temperatures are in the range of 25°-150° C., preferably 30°-60° C., most typically at about 30° C. Typical reaction times vary from about 30 minutes to about 10 hours, preferably 1-5 hours, most typically about 1 hour.

A solvent is not necessary when the pyridine starting material is liquid; however, the quaternization reaction is typically facilitated by the use of a reaction compatible solvent such as an alcohol, glycol, or especially water. Suitable examples include alkanols of 1-8 C-atoms, especially methanol, isopropanol, etc., and the corresponding glycols. The solvent, as usual, will be selected based on considerations of reactant solubilities and desired reaction rates.

If desired, the product quaternary salts can be conveniently isolated using conventional techniques, e.g., by filtration from an alcohol solvent. More typically, the salts are used directly in the next step as aqueous solutions. Yields under all of these conditions are good. For example, yields of the quaternary salts of 4-cyanopyridine and other starting material pyridines are equal to or greater than about 90%.

The relative amounts of reagents are determined in accordance with the usual considerations. Typically, substantially equivalent amounts of the starting material pyridine, the acrylamide reagent and the acid are employed. The amount of solvent, where it is present, is not critical. Typically, the reaction is conducted in the presence of an amount of solvent, e.g., water, which is provided in the commercial forms of the reactants.

The second step nucleophilic displacement is essentially fully conventional. It can be carried out with or without a solvent, under the same considerations as discussed above. Typically, the nucleophilic displacement reactions are carried out in the presence of a reaction compatible base, usually sodium hydroxide. Any other compatible strong base, e.g., having a $pK_b$ equal to or greater than that of potassium carbonate can be used. Other alkali metal hydroxides and carbonates are in this group, as are amidine bases such as 1,5-diazabicyclo[4.3.0]non-5-ene, 1,8-diazabicyclo[5.4.0]undec-7-ene, etc. Suitable solvents include those mentioned above, e.g., they are typically hydroxylic in nature. Suitable reaction times are in the range of −15° to 50° C. In order to maximize yield, it is greatly preferred that the temperature be kept relatively low, e.g., less than 10° C., preferably around 0° C., in order to prevent the reaction from heating up inordinately. Since the subsequent dequaternization reaction is also carried out under basic conditions, if care is not taken, dequaternization can occur at this stage which would have a disadvantageous effect on the yield of the product.

Typical reaction times are in the range of 1 hour to 24 hours. In any given situation, it is preferred that longer times be used rather than shorter times in order to facilitate temperature control and yield maximization. Usually, the pH under which the reaction is conducted is greater than about 11. The amount of base is usually equimolar with the amount of nucleophilic displacement reagent, most often a slight excess (e.g., about 1.25 molar equivalents) of base is used. The amount of nucleophilic displacement reagent is also substantially equimolar with respect to the amount of starting material pyridine. A slight excess (again about 1.25 molar equivalents) of nucleophilic displacement reagent will generally be employed.

A wide variety of nucleophiles commonly employed in aromatic nucleophilic substitution reactions can be used. Among the more common reagents will be primary and secondary amines, $HNR_aR_b$, ammonia, hydrazine, alkylenediamines, (e.g., of 1–8 C-atoms), dialkylenetriamines, (e.g., of 2–16 C-atoms) etc., cycloalkylamines, (e.g., of 3–7 C-atoms), polyethyleneamines, etc. $R_a$ and $R_b$ independently are H, alkyl (e.g., of 1–8 C-atoms), alkenyl, e.g., of 2–8 C-atoms, e.g., allyl, aralkyl (e.g., each of 6–10 C-atoms in the aryl portion and 1–8 C-atoms in the alkyl portion), etc., or together form alkylene of, e.g., 4–8 C-atoms, optionally having an oxa or another N-atom in the resultant ring. In each case these nucleophiles include only those which are compatible and effective with respect to the starting material pyridine. Consequently, in different reactions, the same group can be a nucleophile in one case and a leaving group in another, in dependence upon the routine chemical considerations of nucleophilicity in this regard. Other combinations will be apparent to skilled workers. For example, it has been found that diethanolamine is not suitable for the reaction. Consequently, the alkylamines do not include substituted alkylamines unless, of course, these are equivalent to the alkylamines in their function in the reaction of this invention. Other suitable nucleophiles are O-nucleophiles, e.g., hydroxy, alkoxy, (e.g., of 1–8 C-atoms) e.g., methoxy, etc. In any case, only routine experimentation is required to determine the suitability of a given combination of leaving group and nucleophile.

The dequaternization step is carried out simply by exposing the salt to a sufficiently basic material to cause elimination of the acrylamide starting agent and generate the desired pyridine end product. The quaternary salts typically readily undergo dequaternization in the temperature range of 0°–100° C. depending upon the particular ring substituents involved. Suitable bases are those discussed above in conjunction with the nucleophilic displacement step. Again, solvents are optional; suitable solvents include those discussed with respect to the foregoing steps. Typically, the amount of base will be 1 molar equivalent based upon the starting material salt, the same slight excess generally being used.

In one embodiment of this invention, the nucleophilic displacement reaction and the dequaternization reaction can be carried out at the same time. When this is done, the temperature is generally greater than 10° C. and the yields of the desired pyridine end product are lower than optimal. Consequently, this version of the reaction is not preferred.

The dequaternization step itself is preferably conducted at the higher temperatures in the suitable range, e.g., about 80°–100° C. Further preferably, a relatively large excess of base, e.g., about 1.75 equivalents of sodium hydroxide, is employed. The higher temperature and the higher amount of base effect decomposition of the acrylamide agent which forms during the reaction, with elimination of ammonia. This simplifies the subsequent reaction work-up. At the same time, the higher temperatures help to destroy some of the cyanide ion produced when the preferred 4-cyanopyridine is used as the starting material. This also facilitates work up of the reaction.

All steps of this invention can be carried out batchwise or continuously.

The scheme of this invention for converting one pyridine base into another pyridine base represents a major advance in the field. The intermediary quaternary salts of this invention are stable enough toward dequaternization to allow the mentioned modifications on the pyridine nucleus to prepare the desired new products. Yet, the conditions for the subsequent dequaternization are so mildly basic that this reaction is also carried out under convenient conditions. The special physical properties of the latter reaction and of the system overall, e.g., the great water solubility of all reaction products other than the desired one, represent a clear advantage of this invention over all prior art methods.

All of the products preparable by the process of this invention are useful for known purposes, e.g., as solvents, as commercially useful, compounds, per se, as intermediates for preparing a wide variety of commercial products, etc., or at least as useful for preparing other 4-substituted pyridines which, in turn, have such known uses. More particularly, pyridine compounds, their derived piperidines and their quaternary salts in general exhibit many useful properties which have been exploited in connection with medicinal, agricultural and various other specialty applications such as catalysts for industrial processes and as chemical intermediates. The 4-substituted series in particular occupies an important niche in this scheme. Of the many examples that are readily cited, the following are illustrative.

The 4-dialkylaminopyridines, especially dimethylamine (Steglich et al, Angew Chem. Int. Ed. Engl. 8 981 (1969)), pyrrolidino (Litvinenko et al, Dokl.-Akad.-Nauk SSSR, Ser. Khim, 176, 97 (1967) Chem. Abstr., 68, 68325u (1968)) and 4-(4-methylpiperidino)pyridine (Reilly Report 5, "DMAP Update", Reilly Tar and Chemical Corp., Indianapolis, Ind., 1982), are recognized as uniquely reactive acylation catalysts for the derivatization of unreactive amines and alcohols (Reilly, supra, and G. Hoefle et al, Angew, Chem. Int. Ed. Engl. 17, 569 (1908)). These catalysts also function in the preparation of polyurethanes (British Patent Nos. 990,663 and 990,637 and DOS No. 2,234,508), polyesters (U.S. Pat. No. 4,130,541 and DOS No. 2,643,913 and Brit. Patent No. 1,565,978), polyamides (Brit. Patent No. 1,208,691 and U.S. Pat. No. 4,286,085) and polycarbonates (U.S. Pat. No. 4,286,085). Various quaternary salts of 4-dimethylaminopyridine have been shown to possess fungicidal and bactericidal activity (Badawi et al, Curr. Sci. 52 (24), 1169 (1983)).

4-aminopyridine has been shown to be an effective bird repellant in corn fields where destructive feeding is a problem (Chemtech, 710, Dec. 1982). Pinacidil, obtained formerly by replacing a hydrogen on the 4-amino group with a substituted cyanoguanyl residue, is a vasocactive antihypertensive agent (Olsen et al, EUR. J-Pharmacol 83 (4), 389 (1983)).

A recently reported anxiolytic compound (J. Med. Chem., 26 (5), 621 (1983)) contains a 4-hydroxypiperidine moiety and a potential neuroleptic agent contains an acylated 4-aminopiperidine function (Florvall et al, 20 (5), 365 (1983)). These examples serve as testimony to the wide spectrum of applications possible for this class of compounds. All of them (or intermediates leading to them) can be prepared using the present invention.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

N-(2-carbamoylethyl)-4-cyanopyridinium chloride Isolation of title compound

The following procedure was also applied to the preparation of the 3-cyanopyridine quaternization salt and also to mixtures of 3-cyano/4-cyanopyridine quaternization salts.

A five liter, three-necked round bottom flask was fitted with a mechanical stirrer, thermometer, dropping funnel and a heating mantle. The flask was charged with 637 g of 98% 4-cyanopyridine followed by one liter of isopropanol. Stirring was initiated and 426 g of acrylamide followed by another one liter portion of isopropanol was charged to the flask. The temperature was 6° C. at this point. The dropping funnel was charged with a solution of hydrogen chloride in isopropanol (21.12% w/v) and 1033 ml of this solution was added to the reaction flask over a one hour period. The reactor temperature was 46° C. at this point and a white precipitate had developed. Heat was applied—the dropping funnel was replaced by a reflux condenser and the mixture which became thicker was refluxed for one hour, then allowed to cool overnight. The heavy precipitate was collected on a Buchner funnel by vacuum filtration. This was washed with cold isopropanol and dried in a vacuum oven for two hours at 60° C., affording 1172 g of the title compound with melting point 188°–189° C. Yield 92.6%.

This material was amply pure for further use. An analytical sample was prepared by crystallization from methanol-acetone. It was characterized by combustion analysis, NMR, IR, UV and melting point:

4-Cyanopyridine quaternary salt

Elemental analysis calculated for:
%C, 51 073; %H, 4.762; %N, 19,855; %O, 7.559; %Cl, 16.750.
Found:
%C, 51.45; %H, 4.88; %N, 20.42; %O (by diff.), 6.20; %Cl, 17.05.
mp: 187.00°–188.2° C. (uncorrected).

| UV spectrum: (H$_2$O sol'n) | |
| --- | --- |
| lambda max. | 241 nm |
|  | 2,378 |
| lambda max. | 278.5 nm |
|  | 3,639 |

Infrared spectrum (KBr) cm$^{-1}$: 3340; 3180; 3110; 3060; 3030; 2990; 2940; 2850; 2255; 1725; 1700; 1505; 1455; 1410; 1340; 1245; 1202; 1105; 885 and 730.

H NMR spectrum (90 MHz, CD$_3$OD) ppm: 3.2 (2H, triplet); 5.1 (2H, triplet); 8.6 (2H, doublet); 9.45 (2H, doublet).

3-cyanopyridine quaternary salt,

Elemental analysis calculated for:
%C, 51.073; %H, 4.762; %N, 19.855; %O, 7.559; %Cl, 16.750.
Found:
%C, 50.85; %H, 4.58; %N, 19.49; %O (by diff.), 8.11; %Cl, 16.97.
mp: 190.2°–191.2° C. (uncorrected).

| UV spectrum (H$_2$O): | |
| --- | --- |
| lambda max | 230 nm |
|  | 2,275 |
| lambda max | 269 nm |
|  | 2,774 |

Infrared spectrum (KBr) cm$^{-1}$: 3330; 3170; 3050; 3020; 2980; 2930; 2240; 1680; 1660; 1465; 1450; 1418; 1370; 1300; 1205; 1165; 1118; 850 and 695.

H NMR spectrum (90 MHz, D$_2$O) ppm: 3.75 (2H, triplet); 5.61 (2H, triplet); 8.92 (1H, triplet); 9.6 (1H, doublet); 9.8 (H, doublet); 10.14 (1H, singlet).

EXAMPLE 2

For in situ use

A one liter, three-necked round bottom flask equipped with a dropping funnel, thermometer and magnetic stir bar was charged with 106 g of 98% 4-cyanopyridine and 144 g of commercially available 50% acrylamide solution (assay: 49.3%). Stirring was initiated and 82.4 ml of concentrated hydrochloric acid (assay: 37.5%) was added to the slurry over twelve minutes. The solids gradually dissolved and an exotherm was observed. The resulting solution was allowed to stand at ambient temperature for two hours. It was then usable directly for the preparation of dimethylaminopyridine (DMAP) or other 4-substituted pyridines.

This procedure is also applicable to the preparation of a quaternary salt mixture from a mixture of 3 and 4 cyanopyridines.

(Yields in all cases are near 100%.)

EXAMPLE 3

A total of 182 ml of aqueous dimethylamine solution (assay: 30.9% w/v) was introduced into a two liter three-necked round bottom flask equipped with thermometer, dropping funnel and magnetic stir bar. The flask was then cooled in an ice-methanol bath. When the internal temperature reached 8° C., stirring began and 67.6 ml of 50% sodium hydroxide solution was added dropwise, maintaining the temperature below 10° C. The addition was accomplished in ten minutes. During the entire period of time, the quaternary salt solution prepared in Example 2 was cooled in an ice bath. It was then charged portionwise to a clean dropping funnel. The addition of the quaternary solution was accomplished in 46 minutes, maintaining the reaction temperature of 6°-10° C. A characteristic dark purple color developed. Upon completion of the quaternary salt addition, the reaction mixture was allowed to age for one hour. At this stage, an additional 94.6 ml of 50% sodium hydroxide was added to the reaction mixture, maintaining the temperature below 10° C. This required 16 minutes. The mixture was allowed to stir for another five minutes and was then heated to and maintained at reflux for two hours. The reaction mixture was allowed to cool to room temperature (becoming thick with dark crystalline product) and was extracted four times with half its volume of fresh toluene. The combined extracts were dried over anhydrous sodium sulfate which was filtered and the yellow toluene solution was concentrated to dryness in vacuo. The crude product was further dried in a vacuum oven at 45° C. for one hour. This yielded 95 g of the title compound or product (98% assay by perchloric acid titration) mp. 108.8°-111° C. (uncorrected). This material was further purified by crystallization from toluene. An analytical sample prepared in this way was characterized by its UV spectrum, infrared spectrum, and melting point. In like manner other 4-substituted pyridines were prepared, e.g., 4-dibutylamino, n-octylamino, etc., pyridines.

EXAMPLE 4

As in Example 2, a one liter, three-necked round bottom flask equipped with a dropping funnel, thermometer and magnetic stir bar is charged with 113 g of 4-chloropyridine and 144 g of commercially available 50% aqueous acrylamide solution. Stirring is initiated and 82.4 ml of concentrated hydrochloric acid is added to the mixture over twelve minutes. The resulting solution is allowed to stir at ambient temperature for two hours. This solution containing the 2-carbamoylethyl quaternary salt of 4-chloropyridine is then used directly to prepare dimethylaminopyridine (DMAP) or other 4-substituted pyridine. In like manner the 2-carbamoylethyl salts of 4-bromopyridine, 4-phenoxypyridine, 4-(p-toluenesulfonyl)pyridine and others are prepared and used directly to synthesize DMAP or other 4-substituted pyridine.

EXAMPLE 5

As in Example 3, 182 ml of aqueous dimethylamine solution is introduced into a two liter three-necked round bottom flask equipped with thermometer, dropping funnel and magnetic stir bar. The flask is then cooled in an ice-methanol bath. When the internal temperature reaches 8° C., stirring is initiated and the dropwise addition of 67.6 ml of 50% sodium hydroxide solution begins, maintaining the temperature below 10° C. The addition is accomplished in ten minutes. During the entire period of time, the quaternary salt solution prepared in Example 4, is cooled in an ice bath. It is then charged portionwise to a clean dropping funnel. The addition of the quaternary salt solution is accomplished, maintaining the reaction temperature at 6°-10° C. Upon completion of the quaternary salt addition, the reaction mixture is allowed to age for one hour. At this stage, an additional 94.6 ml of 50% sodium hydroxide solution is added to the reaction mixture, maintaining the reaction temperature below 10° C. The mixture is then heated to and maintained at reflux for two hours. It is then allowed to cool to room temperature and extracted four times with half its volume of fresh toluene. The combined toluene extracts are dried over anhydrous sodium sulfate, filtered and concentrated to dryness leaving the product, DMAP. In like manner, other 4-substituted pyridines are prepared, e.g., 4-dibutylamino, n-octylamino, etc.

EXAMPLE 6

4-dimethylaminopyridine,5, from a mixture of 3-cyanopyridine and 4-cyanopyridine The "aqueous" procedure of Example 2 described above for the preparation of 1-(2-carbamoylethyl)-4-cyanopyridinium chloride was used. The starting mixture contained 56.6 w/w of 4-cyanopyridine and 38.6% w/w of 3-cyanopyridine (184 g: 1 mole of 4-cyanopyridine, 0.68 mole of 3-cyanopyridine). This mixture was reacted with 50% aqueous acrylamide (239 g; 1.68 moles of acrylamide) and concentrated hydrochloric acid (138 ml; 1.68 moles of HCl). Ten percent of the solution of mixed quaternary salts so generated was used directly in the next step.

A 250 ml 3-neck round bottom flask equipped with an addition funnel, thermometer and magnetic stir bar was charged with 30.8% (w/v) of aqueous dimethylamine (30.8 ml; 0.21 mole). This solution was stirred and cooled to 5°-10° C. using an ice water bath. 50% sodium hydroxide (16.8 g; 0.21 mole) was then added slowly to maintain the temperature. Over a period of 35 minutes, 58.5 g of the mixed quaternary solution prepared as described above was added to the reaction solution at a rate which permitted the temperature to be maintained at 5°-10° C. Upon complete addition, the mixture continued to stir at 5°-10° C. for one hour. A second portion of 50% sodium hydroxide was then added dropwise, again maintaining a temperature of 5°-10° C. The addition was complete in 30 minutes and the reaction mixture was brought to reflux and held for two hours. Upon cooling to room temperature the product was extracted using 4 portions of fresh toluene at half the reaction volume. The combined toluene extracts were concentrated to dryness to give 10.4 g of 4-dimethylaminopyridine product, mp. 107°-110° C. This was crystallized from toluene giving 8.8 g of product, mp. 109.5°-112° C., yield 67%. No 3-dimethylaminopyridine was detected, thereby demonstrating the selectivity of the displacement to the 4-cyanopyridine quaternary salt.

EXAMPLE 7

4-pyrrolidinopyridine

To a 250 ml, 3-neck round bottom flask equipped with a thermometer, pressure equalizing addition funnel and magnetic stir bar, was charged 10.6 ml of pyrrolidine (0.125 mole) and 13.5 ml of deionized water. The flask was cooled in an ice water bath and 10 g (0.125 mole) of a 50% (w/w) sodium hydroxide solution was added slowly with stirring. Upon complete addition, the solution was cooled below 5° C.

A solution of 1-(2-carbamoylethyl)-4-cyanopyridinium chloride (21.2 g; 0.1 mole) dissolved in 15 ml of deionized water was prepared and charged to the dropping funnel. This solution was then added to the pyrrolidine/sodium hydroxide solution at a rate which permitted maintenance of the reaction temperature with stirring at below 5° C. It was held there for an additional hour, after which 14 g (0.175 mole) of a 50% (w/w) sodium hydroxide solution was added dropwise with continued maintenance of the reaction temperature below 5° C. (approximately 45 minutes). The mixture was then heated to reflux and maintained for two hours and then allowed to cool.

The aqueous mixture was extracted four times with half its volume of toluene and the combined extracts were concentrated to a residue of 14.7 g which solidified. This crude material was crystallized from ethylacetate to give 4.04 g of the title compound as product, mp. 58°-59° C. (66% yield).

EXAMPLE 8

4-(4-methylpiperidino)pyridine

The exact procedure of Example 5 for the preparation of 4-pyrrolidinopyridine was followed substituting 12.4 g (0.125 mole) of 4-methylpyridine in 18.6 ml of water for the aqueous pyrrolidine solution. After concentration of the toluene extracts, a quantitative yield of the title compound product was obtained as a reasonably pure oil.

EXAMPLE 9

4-aminopyridine 125 g (1 mole) of concentrated ammonium hydroxide was placed in a 500 ml 3-neck round bottom flask equipped with a magnetic stir bar, thermometer and pressure-equalized dropping funnel. The flask was cooled in an ice water bath until the internal temperature was below 50° C.

A solution of 1-(2-carbamoylethyl)-4-cyanopyridinium chloride, (21.2 g; 0.1 mole) in 15 ml of deionized water was then charged to the dropping funnel and added slowly to the stirred ammonia solution. The reaction temperature was maintained below 5° C. during the addition (approximately 23 minutes) and for an additional hour. At this time, 24 g (0.3 mole) of a 50% (w/w) sodium hydroxide solution was added dropwise, continuing to maintain a temperature below 5° C. (approximately 15 minutes). The reaction mixture was then heated to reflux and maintained for two hours. It was allowed to cool and then extracted four times with half volumes of methylisobutyl carbinol. The combined extracts were distilled to dryness and the residue slurried in ethyl acetate. Filtration and drying in vacuo produced 3.8 g of crystalline title compound product; mp. 155°-156° C. (40% yield).

EXAMPLE 10

4-hydroxypyridine

A total of 10.6 g (0.05 mole) of 1-(2-carbamoylethyl)-4-cyanopyridinium chloride in 6.8 ml of water was charged to a 100 ml 3-neck round bottom flask equipped with a magnetic stir bar, thermometer and dropping funnel. The solution was stirred and cooled in an ice-methanol bath. The dropping funnel was charged with 6 g (0.075 mole) of a 50% (w/w) sodium hydroxide solution in an additional 14 ml of water. When the temperature of the quaternary salt solution had reached 8° C., addition of the sodium hydroxide solution began. The reaction temperature continued to drop to −1° C. over the 20 minute addition period. The resulting solution was kept below 10° C. for an additional hour and then 17 ml (0.32 mole) of a 50% (w/w) sodium hydroxide solution was added dropwise over 10 minutes, allowing the temperature to rise. The reaction mixture was brought to reflux and maintained for one hour and fifteen minutes. Upon cooling back down to 8° C., a crystalline solid deposited. This material was recovered by filtration and washed with acetone. After drying, the weight was 7.23 g. This material was slurried in isopropanol and acidified with a solution of hydrogen in isopropanol. The salts were filtered off and the filtrate was concentrated in vacuo leaving an off-white solid, which was the title compound; dry weight 2.73 g (57% yield).

EXAMPLE 11

4-methoxypyridine

A 50 ml round bottom flask equipped with a magnetic stir bar was charged with a solution of 1-(2-carbamoylethyl)-4-cyanopyridinium chloride (1.09 g; 0.005 mole) in 15 ml of methanol. This solution was cooled to 4° C. while stirring and potassium carbonate (0.69 g; 0.005 mole) was added as a solid in one portion. The resulting reaction mixture was maintained at 4° C. for twenty-six hours. At the end of this period, it was neutralized by dropwise addition of trifluoro-acetic acid (0.46 ml; 0.006 mole) and the ensuing solids were filtered. The filtrate was concentrated in vacuo and redissolved in 2 ml of methylene chloride. This solution was extracted with 2 ml of water and then concentrated to a residual liquid weighing 0.265 g. Proton NMR analysis revealed this to be a 75:25 mixture of 4-methyoxypyridine and 4-cyanopyridine, i.e., a 35% yield of 4-methoxypyridine.

As can be seen from the foregoing, a key feature of this invention is the discovery of the unique advantages which can be derived from employing a quaternization/dequaternization scheme using the group —CH$_2$CH$_2$CONH$_2$ and its equivalents for the quaternization. Other methods for quaternizing substituted pyridines with such groups are contemplated as equivalents within the scope of this invention. For example, the alternative method disclosed in U.S. Pat. No. 3,235,449 is one such alternative process applicable in conjunction with pyridine substituted by hydrocarbylthio groups. This method involves reaction of the substituted pyridine with, e.g., a 3-halopropionic acid amide or a similar reagent. However, this reaction does not have the general applicability of the preferred embodiment described above. See, for example, Dowbenko, supra, which discloses that the reaction with 3-halopropionic acid amides is inoperable in conjunction with certain substituted pyridines. The important point is that other known reactions which are adaptable to prepare a substituted pyridine quaternized by a carbonylethyl group are contemplated equivalents for use in conjunction with the process of this invention.

Accordingly, this invention, for example, also relates to a process for preparing a 4-substituted pyridine product from a starting pyridine substituted in the 4-position by a leaving group susceptible to nucleophilic displacement when the starting pyridine is in quaternized form, comprising, quaternizing the starting pyridine with Z—CH$_2$—CH$_2$—CONR$_3$R$_4$, wherein each of R$_3$ and R$_4$ independently is H or $C_{1-8}$-alkyl or together $R_3$ and $R_4$ form $C_{2-7}$-alkylene bonded to the connecting N-atom, and Z is a leaving group whereby the Z—$CH_2$—$CH_2$—$CONR_3R_4$ compound is effective to quaternize the starting pyridine, subjecting the resultant, corresponding quaternized starting pyridine, to a nucleophilic displacement reaction with a reagent which reacts with it to produce the corresponding quaternary salt of the 4-substituted pyridine product, and dequaternizing the latter under effective basic conditions to liberate the 4-substituted pyridine product.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of the formula

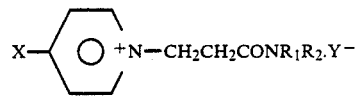

wherein $R_1$ and $R_2$ independently are H or $C_{1-8}$-alkyl or together are $C_{2-7}$-alkylene forming a ring with the connecting N-atom; X is CN, halo, $C_{6-10}$-arylsulfonyl, $C_{6-10}$-arylsulfinyloxy, $C_{6-10}$-aryloxy, $C_{6-10}$-arylthio or $C_{1-8}$-alkysulfonyloxy or nitro, and Y is the anion of an acid having a $pK_a$ of about 3 or less.

2. A compound of claim 1, wherein X is CN.

3. A compound of claim 1, wherein X is CN and $R_1$ and $R_2$ are each H.

4. A compound of claim 2, wherein Y is Cl.

5. A compound of claim 1 wherein X is CN, $C_{6-10}$-arylsulfonyl, $C_{6-10}$-arylsulfinyloxy, $C_{6-10}$-arylthio or $C_{1-8}$-alkylsulfonyloxy or nitro.